United States Patent
Kuchiishi et al.

(10) Patent No.: US 10,087,415 B2
(45) Date of Patent: Oct. 2, 2018

(54) CELL TRAY AND DEVICE, METHOD AND SYSTEM FOR PRODUCING CELL STRUCTURE

(71) Applicant: CYFUSE BIOMEDICAL K.K., Tokyo (JP)

(72) Inventors: Koji Kuchiishi, Tokyo (JP); Tadashi Tamura, Tokyo (JP)

(73) Assignee: CYFUSE BIOMEDICAL K.K., Tokyo (JP)

( * ) Notice: Subject to any disclaimer, the term of this patent is extended or adjusted under 35 U.S.C. 154(b) by 0 days.

(21) Appl. No.: 15/114,970

(22) PCT Filed: Sep. 25, 2015

(86) PCT No.: PCT/JP2015/077056
§ 371 (c)(1),
(2) Date: Jul. 28, 2016

(87) PCT Pub. No.: WO2016/047737
PCT Pub. Date: Mar. 31, 2016

(65) Prior Publication Data
US 2016/0348066 A1   Dec. 1, 2016

(30) Foreign Application Priority Data
Sep. 25, 2014 (WO) .................. PCT/JP2014/075446

(51) Int. Cl.
C12N 5/00 (2006.01)
C12N 11/00 (2006.01)
C12M 1/32 (2006.01)
C12M 1/34 (2006.01)
C12M 3/00 (2006.01)
C12M 1/12 (2006.01)
C12M 1/26 (2006.01)

(52) U.S. Cl.
CPC ........... *C12N 5/0062* (2013.01); *C12M 21/08* (2013.01); *C12M 23/12* (2013.01); *C12M 25/00* (2013.01); *C12M 33/04* (2013.01); *C12M 33/06* (2013.01); *C12M 41/46* (2013.01); *C12N 5/00* (2013.01); *C12N 11/00* (2013.01)

(58) Field of Classification Search
None
See application file for complete search history.

(56) References Cited

U.S. PATENT DOCUMENTS

| | | | |
|---|---|---|---|
| 5,457,041 A | 10/1995 | Ginaven et al. | |
| 2008/0268540 A1* | 10/2008 | Ito | C12M 25/06 435/440 |
| 2008/0299647 A1 | 12/2008 | Ito et al. | |
| 2010/0041143 A1* | 2/2010 | Nishiyama | C12M 23/10 435/375 |
| 2011/0200559 A1 | 8/2011 | Koga et al. | |
| 2014/0120192 A1 | 5/2014 | Nakayama et al. | |

FOREIGN PATENT DOCUMENTS

| | | | |
|---|---|---|---|
| EP | 1997878 | * | 12/2008 |
| EP | 2725091 | * | 4/2014 |
| JP | 2000-23657 A | | 1/2000 |
| JP | 2000-109715 A | | 4/2006 |
| JP | 2008-295376 A | | 12/2008 |
| JP | 2010-200714 A | | 9/2010 |
| JP | 2013-132241 A | | 7/2013 |
| WO | WO 2008/123614 A | | 10/2008 |
| WO | WO 2012/176751 A1 | | 12/2012 |

OTHER PUBLICATIONS

Decision to Grant a Patent (including an English translation thereof) issued in the corresponding Japanese Patent Application No. 2016-504828 dated Apr. 19, 2016.
International Search Report issued in the corresponding International Application No. PCT/JP2015/077056 dated Dec. 8, 2015.
Kawakatsu et al., "Fabrication of Three-dimensional Cell Structures Using Bio-three-dimensional Printing Technology," Journal of Printing Science and Technology, vol. 51, No. 1, Feb. 28, 2014, pp. 18-22 (including a partial English translation thereof).
Notice of Reasons for Rejection (including an English translation thereof) issued in the corresponding Japanese Application No. 2016-504828 dated Mar. 15, 2016.

* cited by examiner

*Primary Examiner* — Thane Underdahl
(74) *Attorney, Agent, or Firm* — Birch, Stewart, Kolasch & Birch, LLP

(57) ABSTRACT

Provided are: a cell tray provided with a concave part for supporting a cell aggregate and a hole formed on the bottom of the concave part; and a device for producing a cell structure, said device being provided with the cell tray and a puncture part passing through the cell tray and the cell aggregate, characterized in that the puncture part passes through the cell aggregate supported by the concave part until the tip thereof intrudes into the hole. Also provided is a system for producing a cell structure, said system comprising: a determination part that examines the characteristics of cell aggregates; a fractionation part that classifies the cell aggregates depending on the results of the examination by the determination part; a discharge part that disposes the cell aggregates in a cell tray depending on the results of the classification by the fractionation part; a puncture part that pass through a plurality of cell aggregates disposed in the cell tray; and a holding part that aligns and holds a plurality of puncture parts passing through a plurality of cell aggregates.

4 Claims, 21 Drawing Sheets

(a)     (b)

(a)          (b)

CELL TRAY AND DEVICE, METHOD AND SYSTEM FOR PRODUCING CELL STRUCTURE

TECHNICAL FIELD

The present invention relates to a cell tray, and a device, a method and a system for producing a three-dimensional cell structure.

BACKGROUND ART

Conventionally, a technique in which a plurality of cell aggregates are stacked to form a three-dimensional structure is known. In this technique, a plurality of cell aggregates that are arranged on a culture plate are picked up and pierced on each of needle-shaped bodies protruding from a support to contact each other. After the cell aggregates have fused with each other, the cell aggregates are pulled out from the needle-shaped body thereby obtaining a three-dimensional cell structure. Various techniques are known for picking up the cell aggregates arranged on a culture plate and pierce them on a needle-shaped body. Patent Document 1 discloses a technique in which a cell aggregate on a culture plate is sucked into a pipette and then transferred to a needle-shaped body, where pressure is applied to the cell aggregate for piercing the cell aggregate on the needle-shaped body, a technique in which a cell aggregate on a culture plate is held and transferred with a small-sized robot arm to be pierced on a needle-shaped body, and a technique in which a cell aggregate on a culture plate is held with tweezers to be pierced on a needle-shaped body. Patent Document 2 discloses a technique in which a cell aggregate on a culture plate is sucked on a tip of a suction nozzle that has a diameter smaller than the diameter of the cell aggregate, and pushed against a needle-shaped body until the needle-shaped body penetrates from the tip to inside of the suction nozzle, thereby piercing the cell aggregate on the needle-shaped body.

RELATED ART

Patent Documents

[Patent Document 1] International Publication No. WO2008123614
[Patent Document 2] International Publication No. WO2012176751

SUMMARY OF THE INVENTION

According to the conventional techniques, however, the step of picking up a cell aggregate from a culture plate through the step of piercing the cell aggregate on a needle-shaped body needs to be carried out as a sequential manner, which requires time. In addition, since the position of the cell aggregate on the culture plate as well as the position of the needle-shaped body are unknown, there is a need for detecting the positions of the cell aggregate and the needle-shaped body by an image recognition technique. In this case, detection result may vary depending on the optical characteristics of the detected object and the lighting conditions, causing increase in the processing time and decrease in yield.

The present invention was made in view of these problems, and has objectives of achieving a cell tray that is capable of easily piercing a plurality of cell aggregates, and a device, a method and a system for producing a cell structure.

A cell tray according to the first invention of the present application is characterized by comprising a concave part configured to support a cell aggregate, and a through part provided at the bottom of the concave part, through which a needle-shaped member can pass. Preferably, the through part comprises a soft material configured to allow a needle-shaped member to pass therethrough. Alternatively, the through part may comprise a hole. The cell tray may further comprise a flat part that is provided at the bottom of the concave part and that has a planar surface substantially perpendicular to the advancing direction of the needle-shaped member. Preferably, the cell tray further comprises a marker configured to indicate the concave part. In addition, the diameter of the hole is preferably smaller than the diameter of the cell aggregate. While a cell aggregate or a mixed cluster of cells and a scaffold material such as collagen may be used, the cell aggregate is preferred. The device for producing a cell structure may further comprise a receiving member configured to hold liquid.

According to the second invention of the present application, the device for producing a cell structure is characterized by comprising a cell tray including a concave part configured to support a cell aggregate and a through part provided at the bottom of the concave part, and a puncturing unit configured to pierce the cell aggregate, and the puncturing unit configured to pierce the cell aggregate supported by the concave part until the tip of the puncturing unit intrudes into the hole.

Preferably, the cell tray comprises a plurality of concave parts and a plurality of through parts, and the puncturing unit that has pierced the cell aggregate is configured to further pierces a cell aggregate disposed in other concave part until the puncturing unit intrudes into the other through part. The through part is a hole which may have a bottom and acylindrical hole. Preferably, the device for producing a cell structure further comprises a receiving member that is configured to hold liquid, wherein the liquid held in the receiving member is configured to enter the concave part. Preferably, the concave part comprises a mortar shape, and the hole comprises a cylindrical shape, wherein the concave part is coaxial with the hole. Preferably, the puncturing unit comprises a plurality of needle-shaped bodies arranged in a line, and the plurality of concave parts are regularly arranged, and the distance between the centers of the adjacent concave parts is equal to the distance between the centers of the adjacent needle-shaped bodies. While a cell aggregate or a mixed cluster of cells and a scaffold material such as collagen may be used, the cell aggregate is preferred.

A method according to the third invention of the present application is characterized by comprising the step of piercing the puncturing unit into a cell aggregate disposed in a concave part until the puncturing unit intrudes into the through part of the cell tray.

A method for producing a cell structure according to the fourth invention of the present application is characterized by comprising the steps of: disposing a cell aggregate into a concave part of the cell tray; and piercing the puncturing unit into the cell aggregate disposed in the concave part until the puncturing unit intrudes into the through part provided at the bottom of the concave part.

Preferably, the concave parts and the through parts are more than one, where the disposing step is a step of disposing a cell aggregate in each of the plurality of concave parts and the piercing step is repeated to further pierce the puncturing unit into a cell aggregate disposed in other concave part. Preferably, the method for producing a cell structure further comprises the steps of: arranging the plurality of puncturing units piercing the plurality of cell aggregates such that the cell aggregates make contact with each other; and pulling the puncturing units out from the cell aggregates after the cell aggregates have fused with each other. Preferably, the method further comprises the step of sorting the cell aggregates, wherein the disposing step is a step of disposing the cell aggregates sorted in the sorting step.

A system for producing a cell structure according to the fifth invention of the present application is characterized by comprising: a determination unit configured to examine a characteristic of a cell aggregate; a sorting unit configured to sort the cell aggregate according to the examination result from the determination unit; a dispensing unit configured to dispose the cell aggregate into the cell tray according to the sorting result from the sorting unit; a puncturing unit configured to pierce the plurality of cell aggregates disposed in the cell tray; and a retaining member configured to arrange and retain the plurality of puncturing units that have pierced the plurality of cell aggregates.

Preferably, the system further comprises a post-processing module comprising an assembling unit configured to house the plurality of retaining members such that the cell aggregates make contact with each other; a first circulating unit configured to circulate liquid inside the retaining member and a second circulating unit configured to circulate liquid outside the retaining member inside the assembling unit. Preferably, the cell tray comprises: a base; a concave part provided in the base and configured to support a cell aggregate; and a through part provided at the bottom of the concave part, wherein the puncturing unit configured to pierce the cell aggregate supported by the concave part until the tip of the puncturing unit intrudes into the through part.

The present invention provides a cell tray that is capable of easily piercing a plurality of cell aggregates, and a device, a method and a system for producing a cell structure.

DESCRIPTION OF REFERENCE NUMERALS

Figure 1:
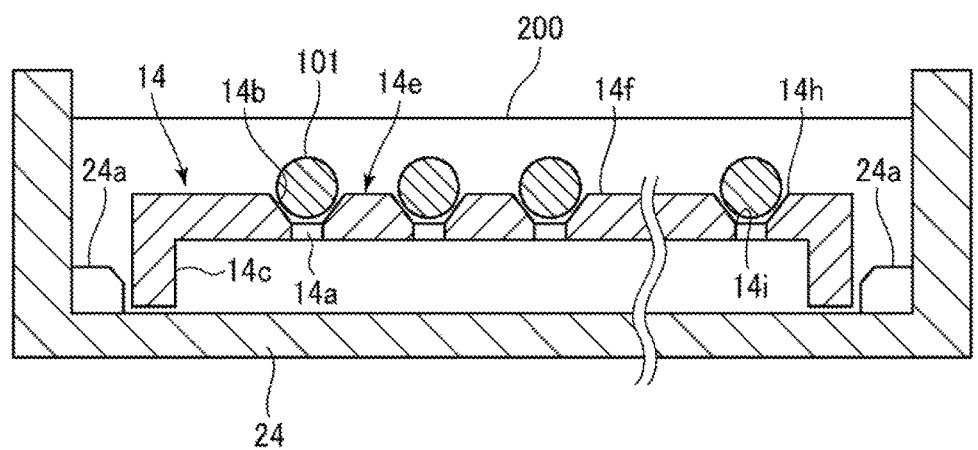
FIG. 1 A cross-sectional view schematically showing a cell tray and a table carrying cell aggregates.

5 Plate
10 Sorter module
11 Cell aggregate feeder
12 Collecting unit
12a Pipetter
12b Cylindrical pipe
12c Pipe supporter
13 Sorter
13a Hopper section
13b Flowing section
13c Determination unit
13d Sorting unit
13e Dispensing unit
14 Cell tray
14a Hole
14b Concave part
14c Leg part
14d ID
14e Base
14f Surface
14g Marker
14h Opening part
14i Bottom part
14j Flat part
14k Through part
15 Magazine
16 Discarding unit
20 Stacking module
21 Needle feeder
21a Needle
21b Needle holder
22 Skewer
22a Chuck
22b Laser oscillator
22c Laser detecter
22d Position determination unit
22e Driver
24 Table
24a Ledge
25 Assembling unit
25a Aligning frame
25b Upper groove
25c lower groove
25d Window part
25e Upper bar
25f Lower bar
25g Side bar
26 Cell stacking unit
30 Post-processing module
31 Culture unit
32 First circulating unit
32a First pump
32b First pipe
33 Second circulating unit 33a Second pump/heater
33b Second pipe

DESCRIPTION OF THE PREFERRED EMBODIMENTS

Figure 2:
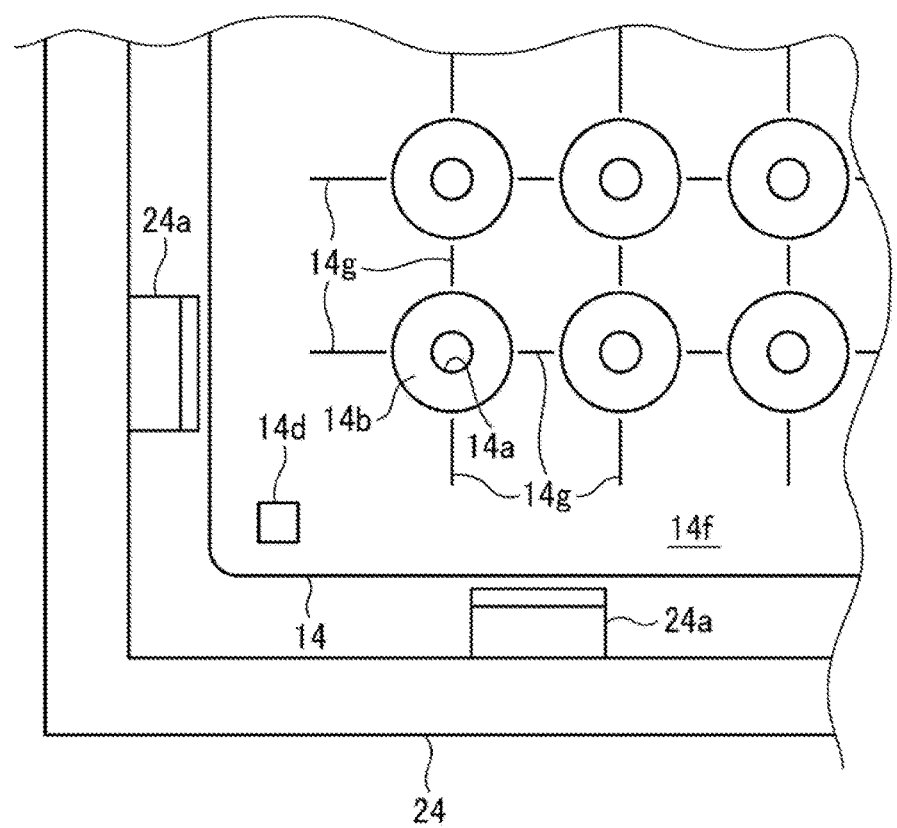
FIG. 2 A partial plan view schematically showing a part of the cell tray and the table.

First, a cell tray 14 and a table (receiving member) 24 according to one embodiment of the present invention will be described with reference to FIGS. 1 and 2.

The cell tray 14 is mainly provided with a base 14e, holes 14a, concave parts 14b and leg parts 14c, where the concave parts 14b are formed in the base 14e, and the holes 14a are provided at the bottom of the concave parts 14b. The base 14e is a rectangular plate, which is made of a non-cell toxic material such as stainless steel. The holes 14a and the concave parts 14b penetrate in the thickness direction of the base 14e. The hole 14a and the concave part 14b serve as a cell support. The concave part 14b, for example, is a mortar shape well, which has a predetermined depth in the thickness direction (for example, substantially half the thickness) of the base 14e from the surface thereof. At the concave part 14b, the opening part 14h that opens at the surface 14f of the base 14e and the bottom part 14i formed inside the base 14e are circular, where the diameter of the opening part 14h is longer than the diameter of the bottom part 14i. The cross-section across the axis of the concave part 14b has a truncated cone shape. The hole 14a has a cylindrical shape, where the diameter of the hole 14a equals the diameter of the bottom part 14i. The cross-section across the axis of the hole 14a has a rectangular shape. The hole 14a and the concave part 14b are formed coaxially. The leg part 14c is formed from the same material as the base 14e, and elongates from the end of the base 14e towards the thickness direction of the base 14e. Accordingly, when the cell tray 14 is placed on the table 24, a space is formed between the bottom surface of the table 24 and the base 14e. Referring to FIG. 2, the concave parts 14b are regularly arranged in a matrix on the surface 14f. In each column, the distances between the centers of the adjacent concave parts 14b are equal.

The surface 14f of the base 14e is provided with an ID 14d and markers 14g. The ID 14d is a code specific to the cell tray 14, which serves as an identifier for individual cell tray 14 and is indicated on the surface 14f. The markers 14g are, for example, four line segments indicated around the concave part 14b on the surface 14f. Two markers 14g are arranged on each of the two straight lines that are orthogonal to the center axis of the concave part 14b and that are orthogonal to each other. As described above, the concave part 14b has a mortar shape while the cell aggregate is substantially spherical. Therefore, when a cell aggregate is disposed in the concave part 14b, the cell aggregate partially fits into the hole 14a and thus the cell aggregate is naturally positioned at the center of the concave part 14b. Moreover, the center of the cell aggregate is substantially at a position where the straight lines connecting the markers 14g meet. Here, the cell aggregate may be a cell aggregate (cell aggregate) or a mixed cluster of cells and a scaffold material such as collagen, while it is preferably a cell aggregate.

The table 24 is a receiving pan with a shape and a size capable of accommodating the entire cell tray 14. The cell tray 14 and a buffer liquid such as a phosphate buffered saline or a culture solution containing a physiologically active substance are placed inside the table 24. The amount of the buffer liquid or the culture solution is an amount that allows the cell tray 14 to be entirely immersed in the buffer liquid or the culture solution so that the cell aggregate does not exposed to air. The table 24 is provided with a plurality of aligning ledges 24a. The aligning ledge 24a has a substantially cuboid shape and protrudes inward from the inner side surface as well as the bottom surface of the table 24. Two at each corner, i.e., a total of eight ledges 24a, are provided. The aligning ledges 24a protruding from the bottom surface of the table 24 has a length such that it engages with the leg part 14c to immobilize the cell tray 14. The length of the aligning ledges 24a protruding from the inner side surface of the table 24 is such that the cell tray 14 can be fixed at a given position inside the table 24. the buffer liquid or the culture solution can easily pass through the hole 14a.

Figure 3:
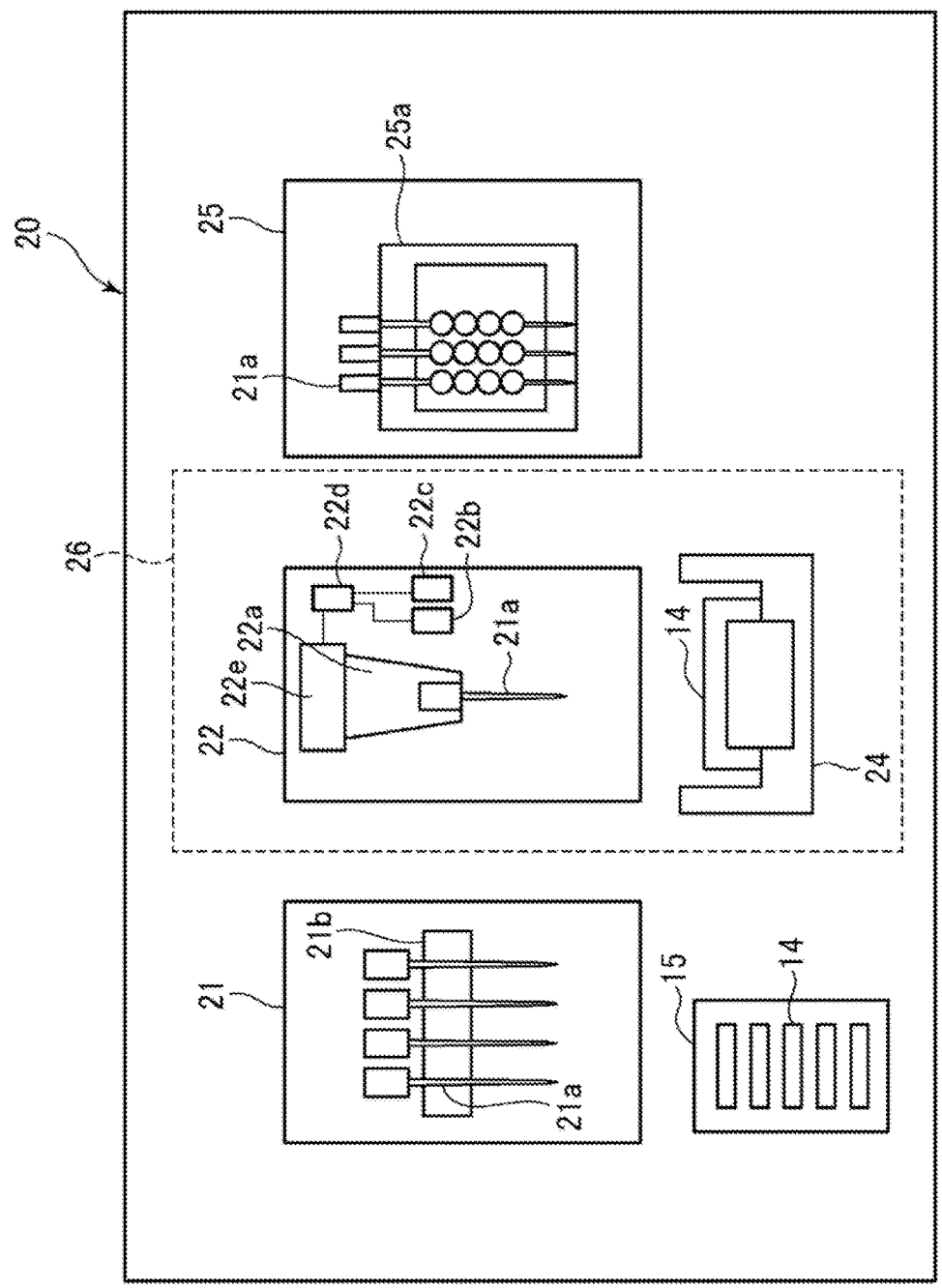
FIG. 3 A block diagram schematically showing a stacking module.

Next, a cell stacking unit (device for producing a cell structure) 26 according to one embodiment of the present invention will be described with reference to FIG. 3.

The cell stacking unit 26 is mainly provided with a cell tray 14, a skewer 22 and a table 24.

The skewer 22 is mainly provided with a chuck 22a, a laser oscillator 22b, a laser detector 22c, a position detection unit 22d and a driver 22e. The chuck 22a picks up and retains a needle 21a from a needle feeder 21 described below. The needle 21a has a conical needle-shaped body that is made from a non-cell adhesive material such as stainless steel. The diameter of the cross-section of the needle 21a can be any diameter that does not disrupt the cell aggregate upon piercing the cell aggregate and that does not prevent fusion of the cell aggregates. For example, the diameter may be 50 micrometers to 300 micrometers. The term "non-cell adhesive" refers to a property that can interfere a cell from adhering via an extracellular adhesion factor. The laser oscillator 22b radiates a laser beam towards the cell tray 14 placed on the table 24. The laser detector 22c receives the light reflected from the cell tray 14. The position detection unit 22d calculates the positional relationship between the needle 21a and the cell tray 14 based on the reflected light, and determines the drive amount of the needle 21a based on the positional relationship. The procedure for calculating the positional relationship will be described below. Based on the drive amount determined by the position detection unit 22d, the driver 22e drives the chuck 22a to stick the needle 21a into the cell aggregate disposed on the cell tray 14. Furthermore, the driver 22e moves the needle 21a piercing the cell aggregate to an assembling unit 25.

Here, the material of the needle 21a and the cell tray 14 is not limited to stainless steel, and may be, but not limited to, other non-cell adhesive material: specifically, a resin such as polypropylene, nylon, a material with a fluorine-coated surface, Teflon (registered trademark), poly-HEMA, an acrylic plate, a vinyl chloride plate, an ABS resin plate, a polyester resin plate or a polycarbonate plate, or an engineering plastic such as PP (polypropylene), ABS (acrylonitrile butadiene styrene), PE (polyethylene), POM (polyacetal), PC (polycarbonate), PEEK (polyether ether ketone), MCN (monomer casting nylon), 6N (6 nylon) and 66N (66 nylon). Besides these materials, a material with a lower cell adhesion property may be used.

Figure 4:
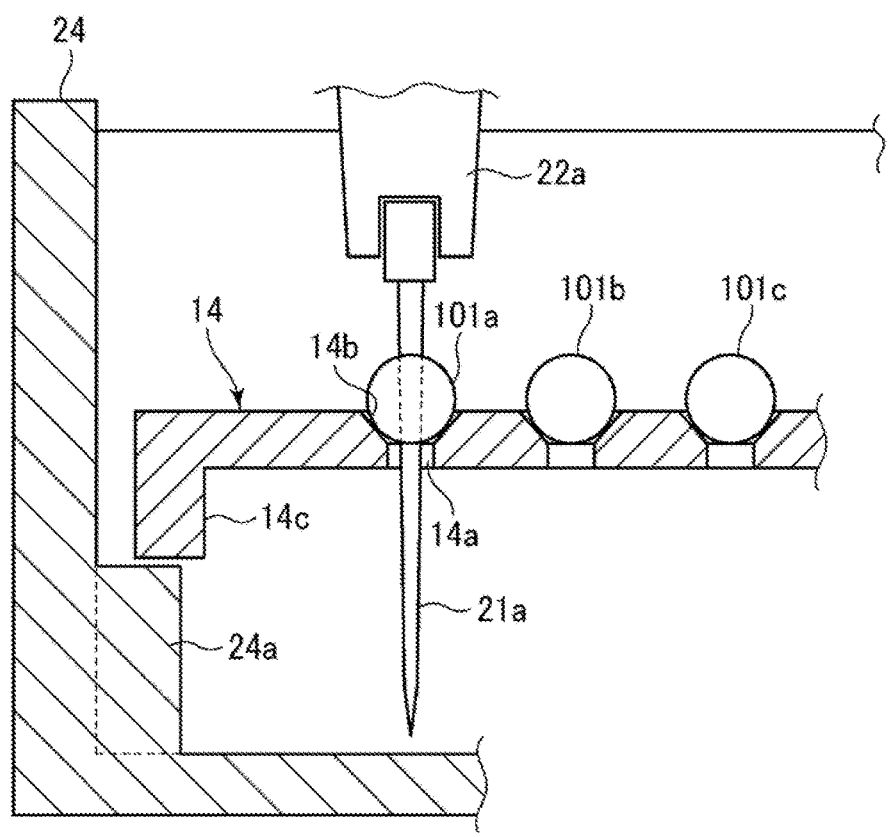
FIG. 4 A view showing a step of piercing cell aggregates.
Figure 5:
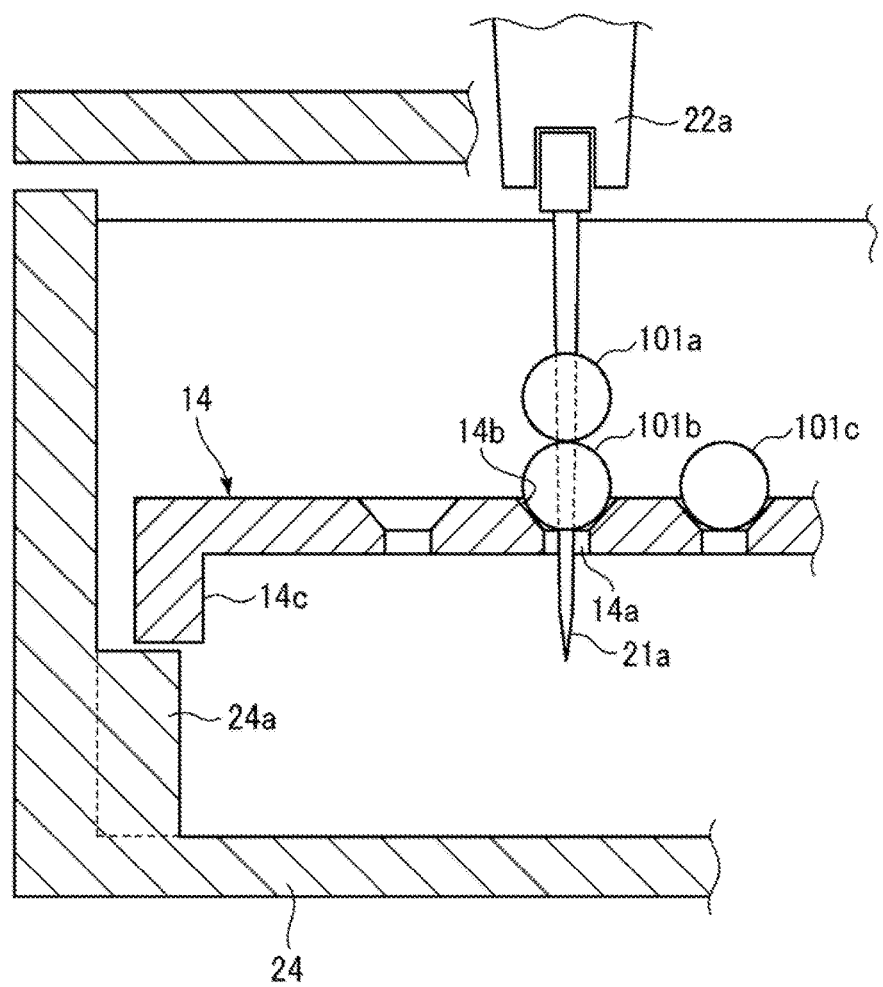
FIG. 5 A view showing the step of piercing cell aggregates.
Figure 6:
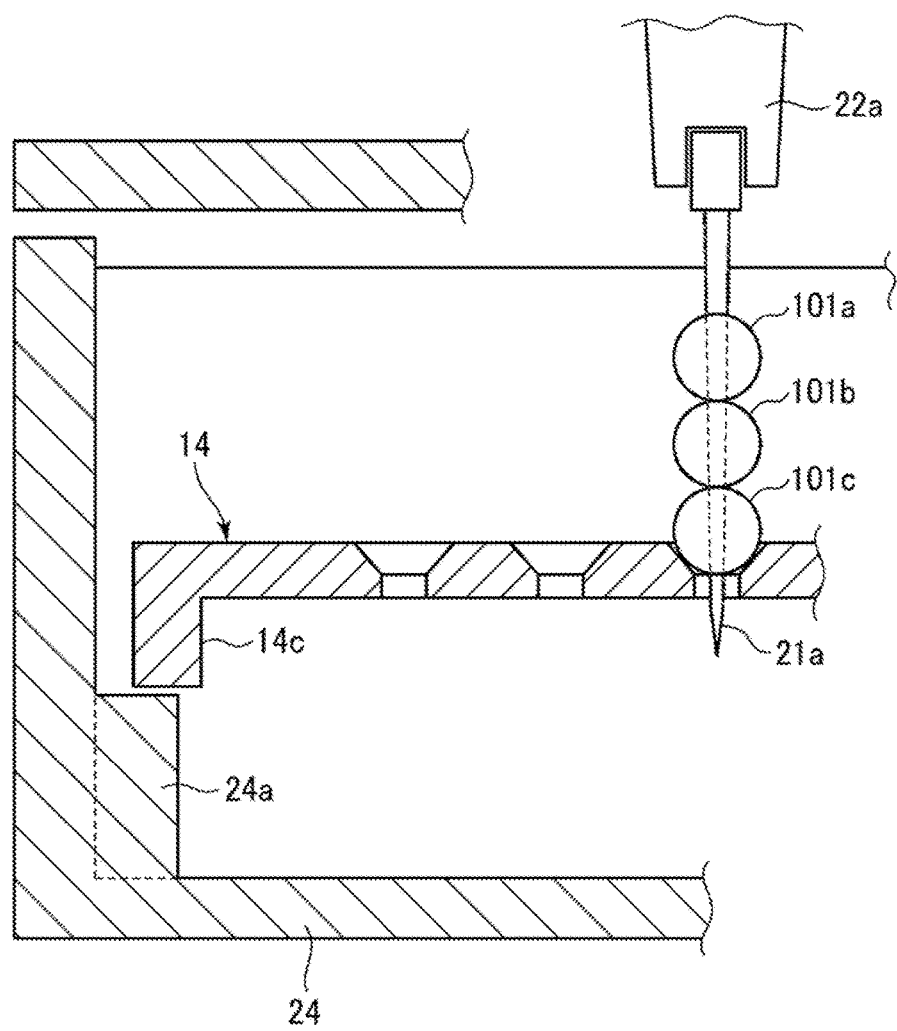
FIG. 6 A view showing the step of piercing cell aggregates.

Next, with reference to FIGS. 4 to 6, the process for the needle 21a to pierce a plurality of cell aggregates will be described. In the following description, the aligning ledges 24a are provided between the edge of the leg part 14c and the bottom of the table 24. First, the laser oscillator 22b irradiates a laser beam toward the cell tray 14 placed on the table 24. Then, the laser detector 22c receives the light reflected from the cell tray 14. The position detection unit 22d confirms the position of the marker 14g based on the luminance of the reflected light, by which calculates the positional relationship between the needle 21a and the cell tray 14. Then, the position detection unit 22d determines the drive amount of the needle 21a based on the calculated positional relationship. The driver 22e drives the chuck 22a based on the drive amount determined by the position detection unit 22d to move the needle 21a immediately above the cell aggregate 101a disposed on the cell tray 14. Subsequently, the driver 22e lowers the needle 21a toward the cell aggregate 101a to pierce the cell aggregate 101a. As the needle 21a is lowered for a predetermined length, the tip of the needle 21a intrudes into the hole 14a. By providing the hole 14a, the needle 21a can pierce the cell aggregate 101a only for the predetermined length. After lowering the needle 21a for a predetermined length, the driver 22e raises the needle 21a. At this point, the needle 21a is stuck in the cell aggregate. Then, the laser oscillator 22b, the laser detector 22c, the position detection unit 22d and the driver 22e again conduct the same processes as described to move the needle 21a immediately above the next cell aggregate 101b to pierce the next cell aggregate 101b (see FIG. 5). By repeating these processes for desired times, a desired number of cell aggregates can be pierced into the needle 21a (see FIG. 6). The amount of lowering the needle 21a toward the cell aggregate is determined according to the size of the cell aggregates and the number of the cell aggregates to be pierced, that is, according to the position of the cell aggregates on the needle 21a. Specifically, the lowering length is the longest when the first cell aggregate is pierced with the needle 21a, and the lowering length becomes slightly shorter than the diameter of the next cell aggregate. By slightly shortening the lowering length, the cell aggregates contact to each other and thus can easily be fused with each other. By repeating these processes, a plurality of needles 21a each piercing a plurality of cell aggregates can be obtained. Here, the first cell aggregate may be pierced for a shorter lowering length, i.e., shallower, than the lowering length shown in FIG. 4, and the lowering length may be determined such that the first cell aggregate is further moved by the subsequently pierced second cell aggregate. After piercing the desired number of cell aggregates with the needle 21a, the driver 22e moves the needle 21a piercing the cell aggregates to the assembling unit 25 described below.

Next, a system for producing a cell structure according to one embodiment of the present invention will be described with reference to FIGS. 7 to 14. The system for producing a cell structure is mainly provided with a cell tray 14, a sorter module 10 (see FIG. 7), a stacking module 20 and a post-processing module 30 (see FIG. 8).

Figure 7:
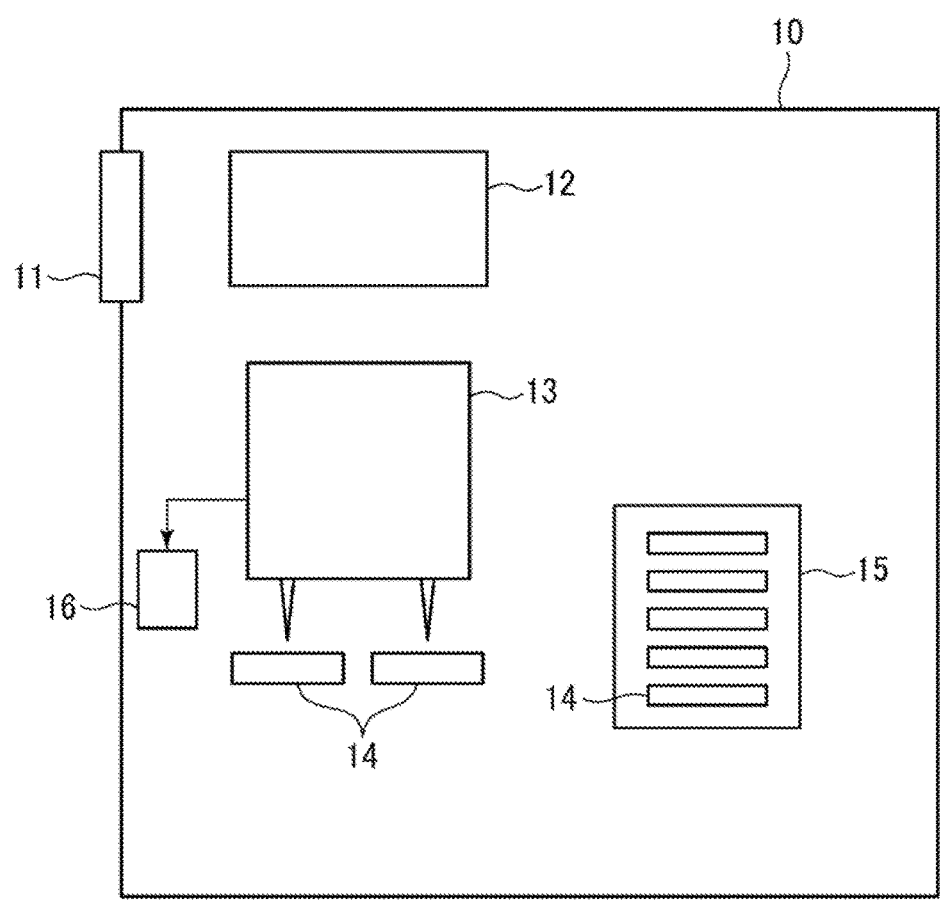
FIG. 7 A block diagram schematically showing a sorter module.

Referring to FIG. 7, the sorter module 10 will be described. The sorter module 10 is mainly provided with a cell aggregate feeder 11, a collecting unit 12, a sorter 13, a cell tray 14, a magazine 15 and a discarding unit 16, and has a function of disposing cell aggregates into the cell tray 14.

The cell aggregate feeder 11 incorporates a plate 5 placed with cell aggregates from outside the sorter module 10. The plate 5 will be described below. The magazine 15 houses a plurality of cell trays 14. The cell tray 14 housed in the magazine 15 is transported with a feeder (not shown) to the sorter 13.

Figure 9:
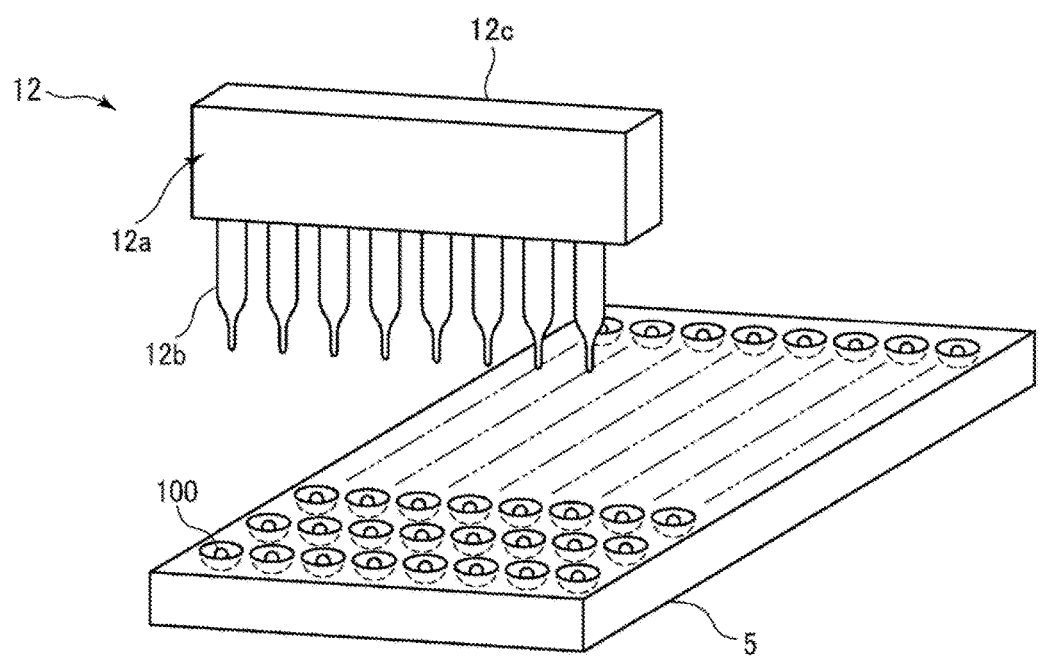
FIG. 9 A perspective view schematically showing a collecting unit.

The collecting unit 12 will be described with reference to FIG. 9. The collecting unit 12 is mainly provided with a pipetter 12a and a plate 5. The pipetter 12a is mainly provided with a plurality of cylindrical pipes 12b whose tip parts has a diameter larger than the diameter of the cell aggregate, and a pipe supporter 12c for arranging and supporting the plurality of cylindrical pipes 12b in a line at regular intervals. A plurality of concaves are formed at regular intervals on the plate 5. The distance between the concaves and the distance between the cylindrical pipes 12b are the same. Cells disposed, on the plate 5 will aggregate with each other with time to form a cell aggregate 100, and settle in these concaves. The end of the cylindrical pipe 12b opposite to the tip part is applied with a negative pressure. With the force of this negative pressure, the tip part of the cylindrical pipe 12b suck up the cell aggregate 100 disposed on the plate 5. Specifically, the pipette suctions to dispose the cell aggregate 100 on the tip part. The pipetter 12a having the cell aggregate 100 at the tip part of the cylindrical pipe 12b feeds the cell aggregate 100 into the sorter 13.

Figure 10:
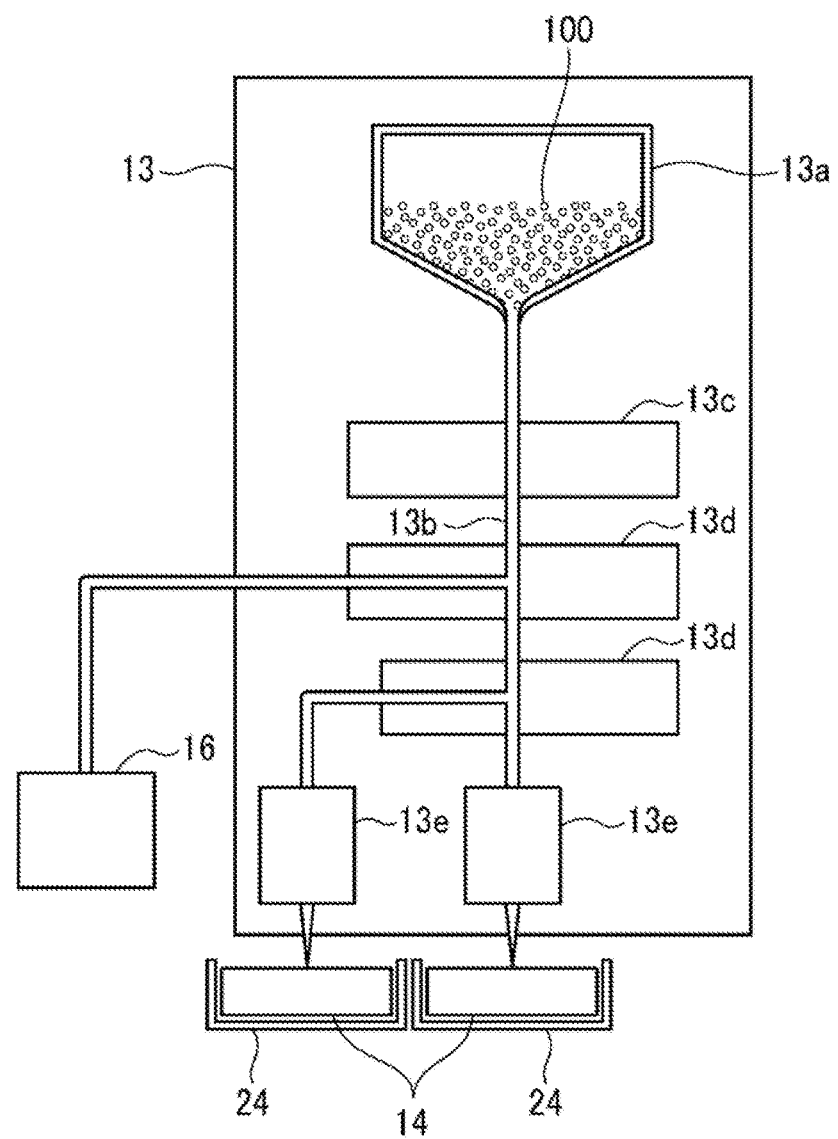
FIG. 10 A block diagram schematically showing a sorter.

The sorter 13 will be described with reference to FIG. 10. The sorter 13 is mainly provided with a hopper section 13a, a flowing section 13b, a determination unit 13c, a sorting unit 13d and a plurality of dispensing units 13e, and has a function of examining and sorting the cell aggregate 100 incorporated from the hopper section 13a according to the characteristic thereof. The characteristic of the cell aggregate 100 may be the size, the shape and the survival rate of the cell aggregate 100. The hopper section 13a has a funnel, and incorporates and accumulates the cell aggregates 100 from the pipetter 12a via the port of the funnel. The flowing section 13b is a pipe with an inner diameter that allows the cell aggregates 100 to pass through, and connects the leg of the funnel with the determination unit 13c, the sorting unit 13d, the dispensing unit 13e and the discarding unit 16. The determination unit 13c tests and determines the characteristic of the cell aggregate 100 and culture solution. The sorting unit 13d sends the cell aggregate 100 to the discarding unit 16 or the plurality of dispensing units 13e according to the determination result from the determination unit 13c. Specifically, the cell aggregates 100 are sorted by the determination unit 13c and the sorting unit 13d. The dispensing unit 13e disposes the cell aggregates 100 on the concave parts 14b of the cell tray 14. The discarding unit 16 houses the cell aggregate 100 received from the sorting unit 13d.

The stacking module 20 will be described with reference to FIG. 3. The stacking module 20 is mainly provided with a needle feeder 21, a skewer 22, a table 24 and an assembling unit 25. The needle feeder 21 is mainly provided with a plurality of needles 21a having a puncturing unit or a needle-shaped body and a needle holder 21b. The needle holder 21b retains the plurality of needles 21a. The cell tray 14 housed in the magazine 15 is placed on the table 24 with a tray feeder (not shown) and carried beneath the skewer 22.

Figure 11:
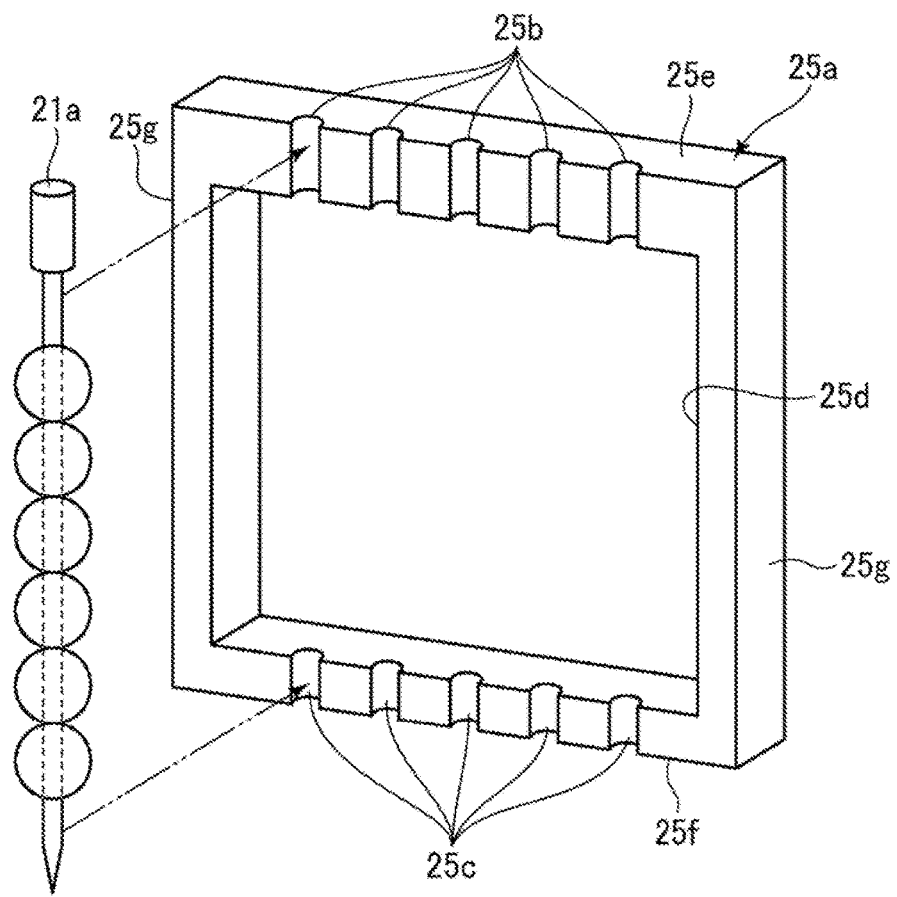
FIG. 11 A perspective view schematically showing an aligning frame.
Figure 12:
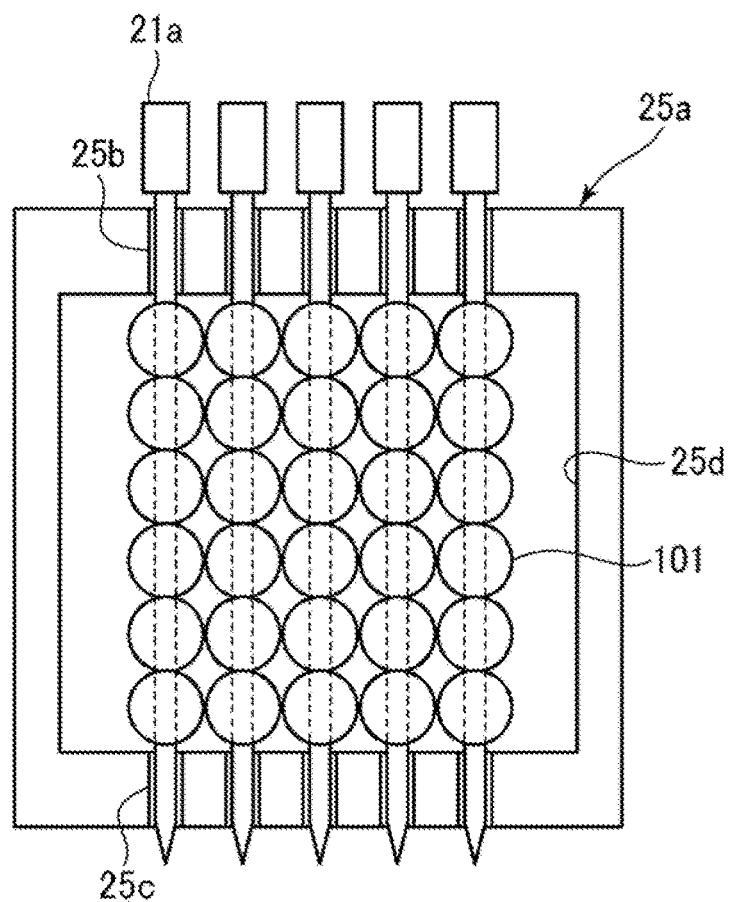
FIG. 12 A plan view showing an aligning frame placed with needles piercing cell aggregates.
Figure 13:
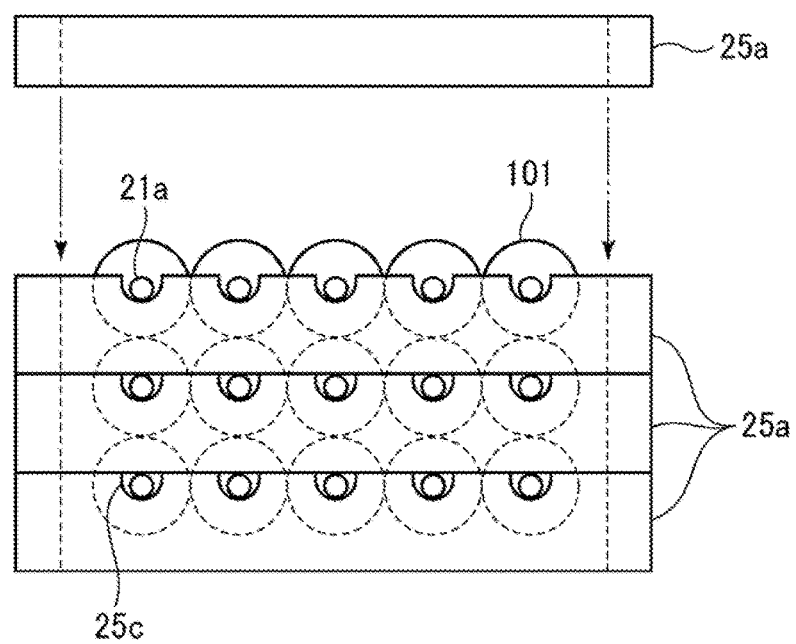
FIG. 13 A side view showing stacked aligning frames.
Figure 14:
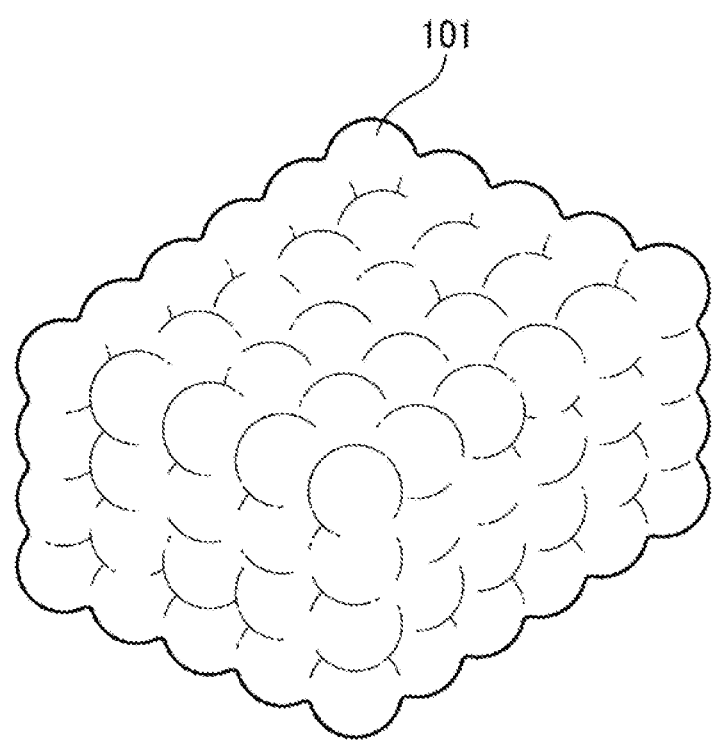
FIG. 14 A perspective view of a three-dimensional cell structure.

The assembling unit 25 will be described with reference to FIGS. 11 to 13. The assembling unit 25 is provided with an aligning frame 25a that serves as a retaining member. The aligning frame 25a is a rectangular frame that is provided with a first bar 25e, a second bar 25f, two side bars 25g, a plurality of first grooves 25b and a plurality of second grooves 25c. The first bar 25e, the second bar 25f and the side bar 25g have cuboid shapes. The lengths of the first bar 25e and the second bar 25f are the same, while the lengths of the two side bars 25g are the same. The first bar 25e, the second bar 25f and the side bars 25g have an expandable mechanism that allows expansion in the longitudinal direction, for example, a telescopic mechanism. Therefore, the lengths of the first bar 25e, the second bar 25f and the side bars 25g may appropriately be determined according to the size of the three-dimensional cell structure produced. The first grooves 25b are grooves with circular arc-shaped cross-sections, which are provided on one side of the first bar 25e. The second grooves 25c are grooves with circular arc-shaped cross-sections, which are provided on one side of the second bar 25f. The numbers of the first grooves 25b and the second grooves 25c are the same, while the axes of the first grooves 25b and the second grooves 25c coincide. The distance between the adjacent first grooves 25b is the same as or slightly shorter than the diameter of the cell aggregate. The same also applies to the second grooves 25c. Accordingly, the cell aggregates make close contact with each other and thus can easily be fused with each other. Using an expandable mechanism similar to the one described above, the distance between the adjacent first grooves 25b and the second grooves 25c can be changed according to the diameter of the cell aggregate. The number of the first grooves 25b and the second grooves 25c may appropriately be determined according to the size of the three-dimensional cell structure produced. The first bar 25e, the second bar 25f and the two side bars 25g form a rectangular window part 25d inside the aligning frame 25a. The needle 21a that has pierced a plurality of cell aggregates is loosely fitted into the first groove 25b and the second groove 25c. FIG. 12 shows a state where the needles 21a are loosely fitted into all of the first grooves 25b and the second grooves 25c. Referring to FIG. 13, the aligning frames 25a are stacked in the thickness direction within the assembling unit 25. The number of the stacked aligning frames 25a may appropriately be determined according to the size of the three-dimensional cell structure produced. After stacking a desired number of aligning frames 25a, an aligning frame 25a without any loosely fit needle 21a is stacked on so as to fix all of the needles 21a in the aligning frame 25a.

Figure 8:
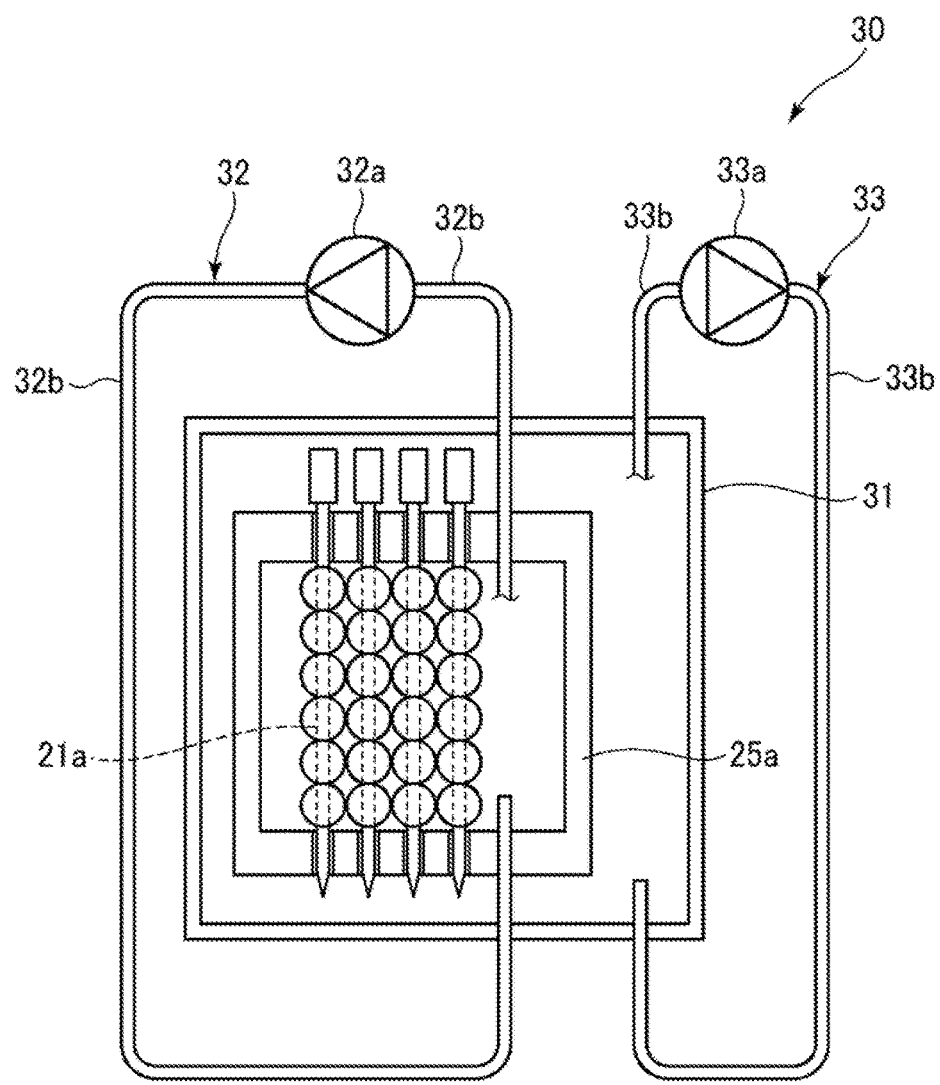
FIG. 8 A block diagram schematically showing a post-processing module.

Next, the post-processing module 30 will be described with reference to FIG. 8. The post-processing module 30 is mainly provided with a culture unit 31, a first circulating unit 32 and a second circulating unit 33. The culture unit 31 houses the plurality of aligning frames 25a that have been stacked in the assembling unit 25. The first circulating unit 32 is provided with a first pump 32a and a first pipe 32b. The first pump 32a is connected to the inside of the aligning frame 25a via the first pipe 32b to circulate the buffer liquid or the culture solution. Since the buffer liquid or the culture solution contains nutrients, oxygen or the like, the cell aggregate positioned inside the aligning frame 25a can be fused without death. The second circulating unit 33 is provided with a second pump/heater 33a and a second pipe 33b. The second pump/heater 33a is connected to the inside of the culture unit 31 outside the aligning frame 25a via the second pipe 33b to circulate a temperature-retaining liquid while maintaining the liquid to stay at a constant temperature. By circulating the temperature-retaining liquid, the cell aggregates can be maintained at a given temperature. After a predetermined period of time in this state, the cell aggregates fuse with each other. Thereafter, all of the needles 21a are pulled out the cell aggregates while keeping the cell aggregates housed in the aligning frame 25a, thereby obtaining a complete three-dimensional cell structure 101 in the aligning frame 25a (see FIG. 14).

According to the invention of the present application, a large number of cell aggregates can easily and rapidly be pierced to rapidly obtain a three-dimensional cell structure with any shape.

Moreover, by using the cell tray of the invention of the present application, a cell aggregate can easily be disposed at a specific position. In addition, the marker 14g can be used to easily specify the position of a cell aggregate, by which the cell aggregate can rapidly be pierced with a needle.

Figure 15:
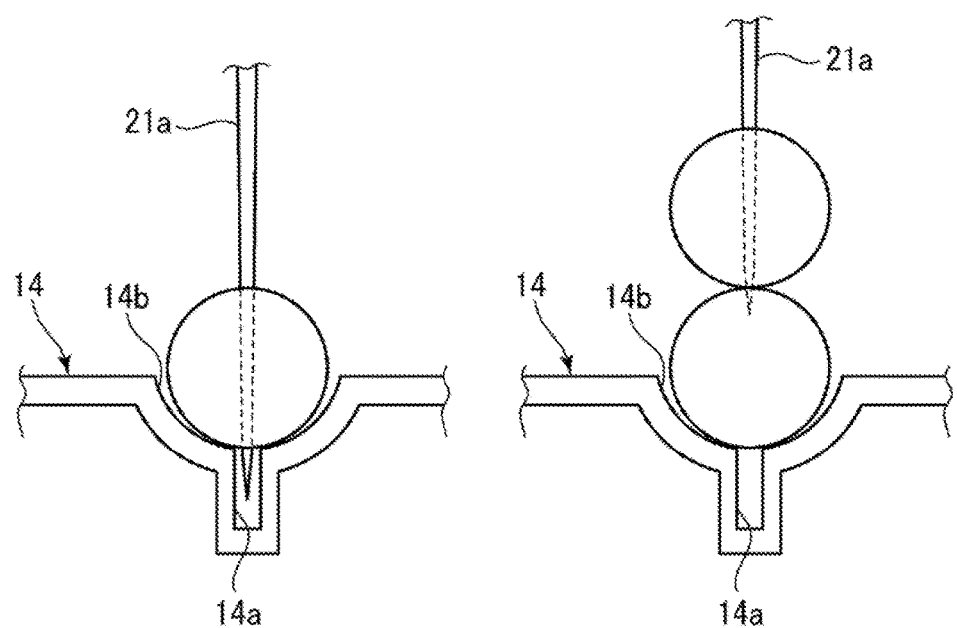
FIG. 15 An end face view schematically showing a cell tray.

In the cell tray 14, the hole 14a may not run through the base 14e in the thickness direction thereof, and may have a bottomed cylindrical shape (see FIG. 15). The depth of the hole 14a has a length that does not allow the tip of the needle 21a to touch the bottom of the hole 14a as the needle 21a is lowered for a predetermined length. By providing the hole 14a, the needle 21a can be pierced into the cell aggregate 101a only for a predetermined length.

Figure 19:
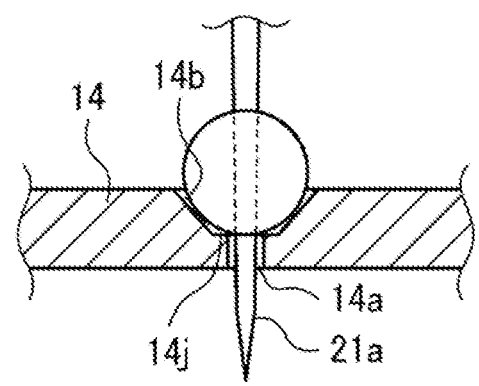
FIG. 19 A partial cross-sectional view of the cell tray.
Figure 20:
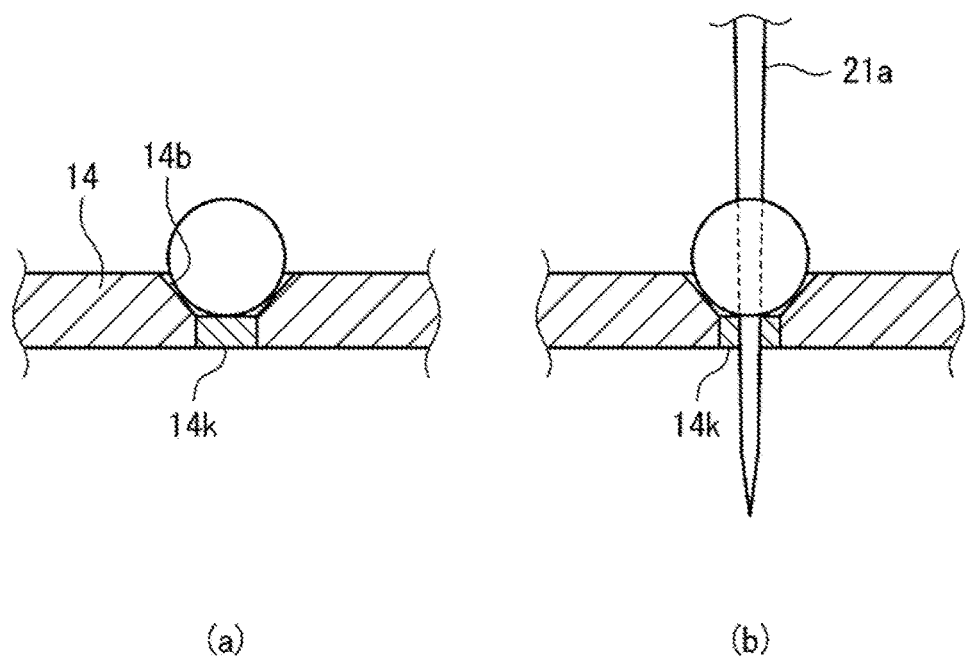
FIG. 20 Partial cross-sectional view of the cell tray.
Figure 21:
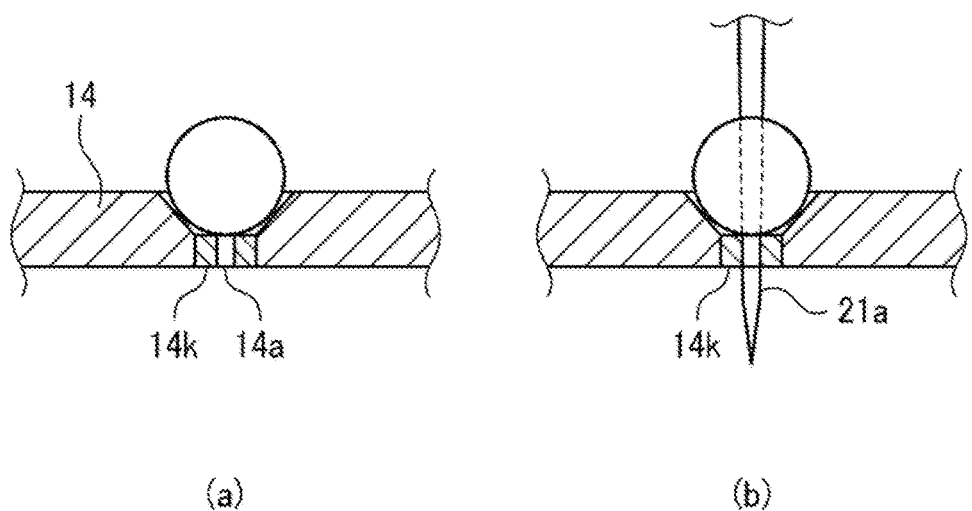
FIG. 21 Partial cross-sectional view of the cell tray.

In the cell tray 14, a flat part 14j with a substantially horizontal planar surface may be provided between the hole 14a and the concave part 14b (see FIG. 19). Here, substantially horizontal means a direction that is substantially perpendicular to the advancing direction of the needle. The flat part 14j supports the cell aggregate in the direction opposite to the advancing direction of the needle 21a as the needle 21a pierces the cell aggregate. This can decrease the possibility of the cell aggregate to be dragged by the needle 21a into the hole 14a. Additionally, a through part 14k made from a soft material that allows the needle 21a to pierce therethrough can be provided at the bottom of the concave part 14b (see FIG. 20). The soft material may, for example, be a sponge, a rubber, urethane, silicone or the like. As the needle 21a pierces a cell aggregate, the through part 14k supports the cell aggregate in the direction opposite to the advancing direction of the needle 21a. The needle 21a that has pierced through the cell aggregate further pierces the through part 14k. This can decrease the possibility of the cell aggregate to be dragged by the needle 21a into the cell tray 14. Additionally the through part 14k can be provided with a hole 14a (see FIG. 21). In this case, the inner diameter of the hole 14a may be smaller or larger than the outer diameter of the needle 21a. When the inner diameter of the hole 14a is smaller than the outer diameter of the needle 21a, the needle 21a that has pierced through the cell aggregate spreads out the hole 14a and further pierces through the through part 14k. As the needle 21a pierces a cell aggregate, the through part 14k supports the cell aggregate in the direction opposite to the advancing direction of the needle 21a. This can decrease the possibility of the cell aggregate to be dragged by the needle 21a into the cell tray 14.

Figure 16:
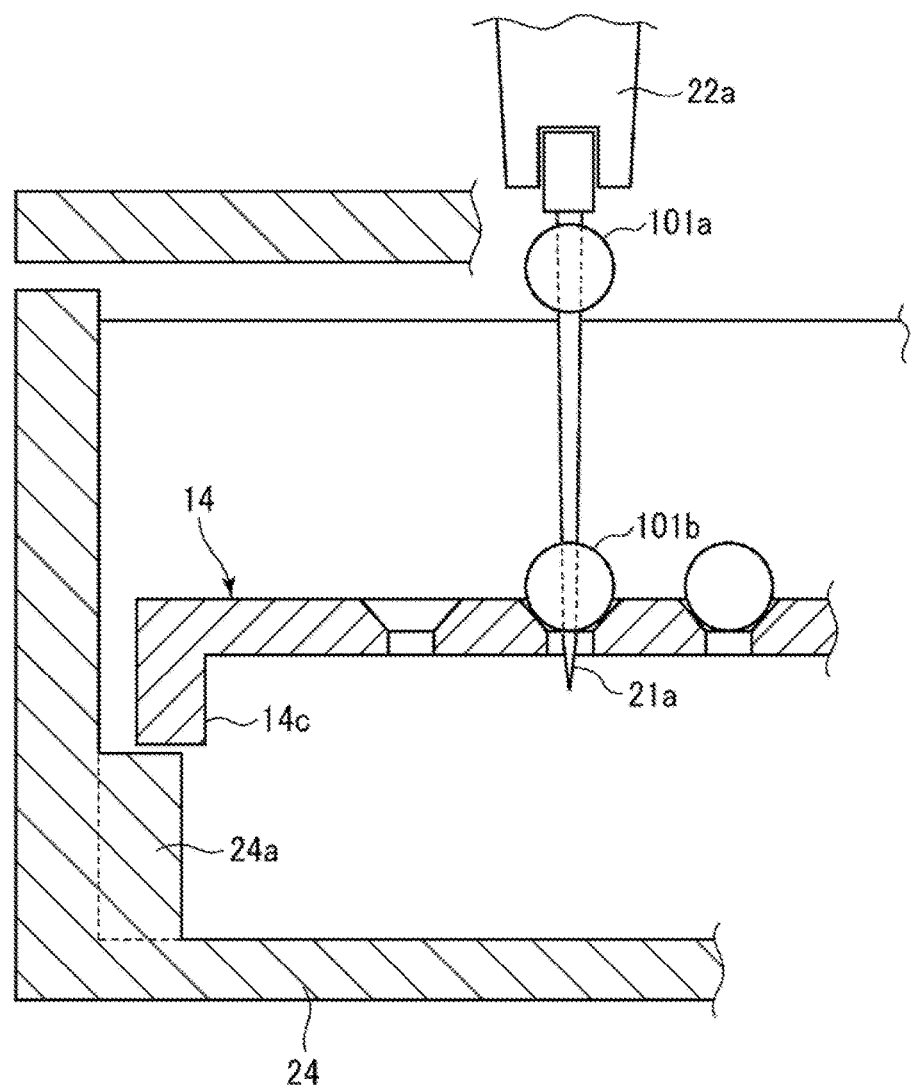
FIG. 16 A view showing a step of piercing cell aggregates.
Figure 17:
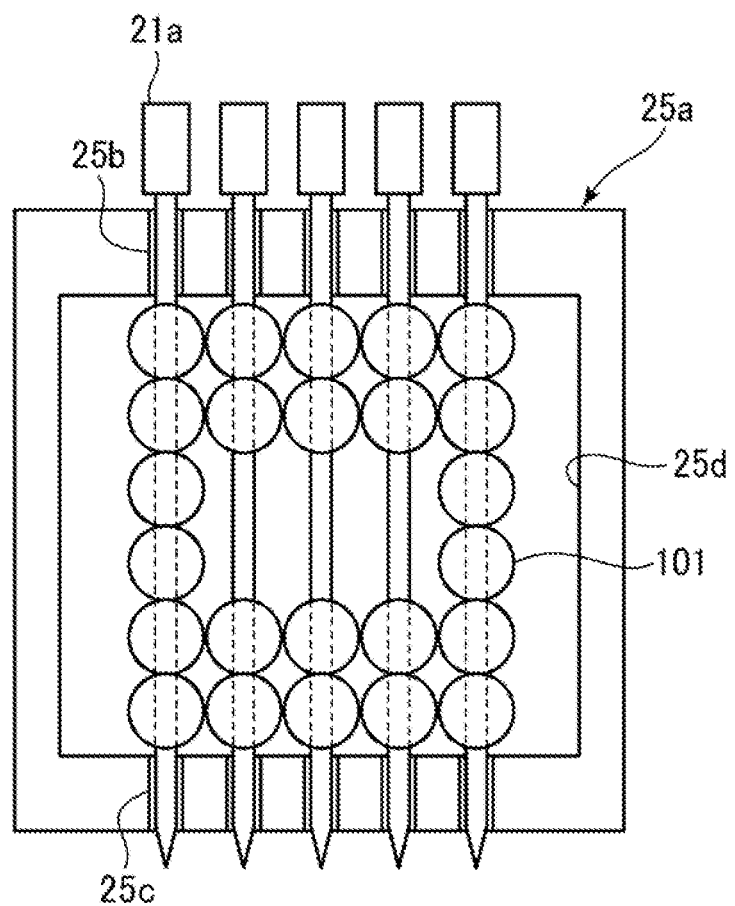
FIG. 17 A plan view showing an aligning frame placed with needles piercing cell aggregates.
Figure 18:
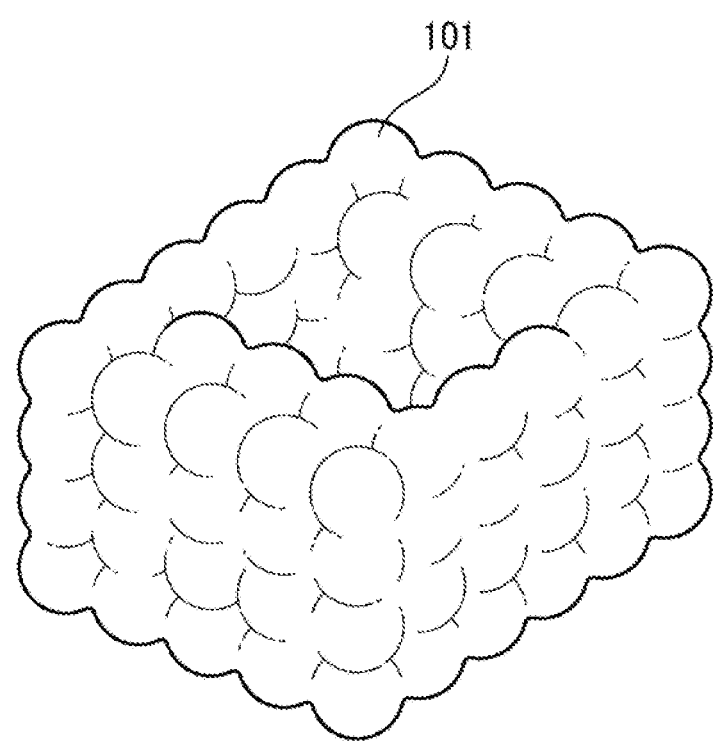
FIG. 18 A perspective view of a three-dimensional cell structure.

According to the present invention, the position of the cell aggregate to be pierced with the needle 21a can be controlled to produce a cell structure with any shape. For example, with reference to FIG. 16, the device for producing a cell structure can also produce a three-dimensional cell structure having a hollow structure. The shape and the size of the hollow structure may arbitrary be designed. For example, a wall surface can be formed with cell aggregates with a hollow inside to produce a cylindrical (tunnel-like) three-dimensional cell structure. When a three-dimensional cell structure produced has a hollow structure, the lowering length of the needle 21a toward the cell aggregate is determined according to the size of the hollow structure. Specifically, the lowering length is decreased for a length corresponding to the size of the hollow structure. This allows a space to be provided for a length corresponding to the size of the hollow structure between the cell aggregate 101a and the cell aggregate 101b. The resultants are arranged in the aligning frame 25a (see FIG. 17), and cultured in the post-processing module 30 for a predetermined period of time, thereby producing a three-dimensional cell structure having a hollow structure. In a case where a three-dimensional cell structure with a hollow structure is produced, the first circulating unit 32 is capable of delivering nutrients, oxygen or the like contained in the buffer liquid or the culture solution to the cells inside the cell aggregate via the hollow structure. This allows production of a three-dimensional cell structure with a larger volume.

The lengths of the concave part 14b and the hole 14a in the axial direction are not limited to the above-mentioned lengths.

Furthermore, the hole 14*a* may not be produced and instead the concave part 14*b* may run through the base 14*e* in the thickness direction. In other words, the concave part 14*b* may also serve as a hole.

The plurality of needles may be used simultaneously. Specifically, each of the plurality of needles can pierce the cell aggregates at the same time. This allows shortening of the time required for piercing all of the cell aggregates. In this case, the distance between the centers of the adjacent concave parts 14*b* is equal to the distance between the centers of the adjacent needle-shaped bodies.

The number of the aligning ledges 24*a* is not limited to the above-mentioned number and may be any number that allows the cell tray 14 to be fixed at a given position in the table 24.

The shapes of the opening part 14*h* and the bottom part 14*i* of the concave part 14*b* are not limited to a circle, and may be rectangle, an eclipse or other shape. The diameter of the hole 14*a* and the diameter of the bottom part 14*i* may not be the same as long as the concave part 14*b* and the hole 14*a* run through. Additionally, the hole 14*a* does not have to have a cylindrical shape.

The three-dimensional cell structure may consist only of the same type of cells or may contain multiple types of cells. The same type of cells refer to functionally equivalent cells that are derived from the same tissue or organ of the same species. A cell construct containing multiple types of cells can be obtained by applying cell aggregates that are formed from different types of cells (for example, cell aggregate A made from cells a and cell aggregate B made from cells b) to the invention of the present application. Here, cells a and cells b may be any cells as long as these cell aggregates can fused with each other. Cells a and cells b may be, for example, cells derived from different tissues (or organs) of the same species, cells derived from the same tissues (or organs) of different species, or cells derived from different tissues (or organs) of different species. Moreover, the number of different types of cells used is not limited to two, and three or more types of cells may be used. The cell aggregate may contain one or more types of cells. In this case, the three-dimensional cell structure may be produced by using only a cell aggregate that contains one type of cells, may be produced by using a plurality of cell aggregates that respectively consist of different types of cells, may be produced by using only a cell aggregate that contains multiple types of cells, or may be produced by using a cell aggregate that contains one type of cells and a cell aggregate that contains different types of cells.

While a number of embodiments of the present invention have been described with reference to the attached drawings, it is obvious for those skilled in the art that modification can be applied to the structure and relationship of each component without departing from the scope and the spirit of the claimed invention.

The invention claimed is:

1. A method for producing a cell tissue structure comprising the steps of:
   providing a cell tray having a concave part to hold a cell aggregate in which a plurality of cells is aggregated and a through part, the through part provided at a bottom of the concave part so that a needle can penetrate the cell aggregate;
   disposing a cell aggregate in the concave part;
   piercing the needle into the cell aggregate disposed in the concave part of the cell tray so that the cell aggregate is skewered and held on the needle.

2. The method for producing a cell tissue structure according to claim 1, wherein
   the cell tray has a plurality of the concave parts each having the through part at the bottom thereof;
   a cell aggregate is disposed in each of the plurality of concave parts; and
   the cells are pierced by the needle so that the cell aggregates are skewered and held on the needle.

3. The method for producing a cell tissue structure according to claim 2, wherein
   a plurality of the needles each holding a plurality of cells are obtained, and
   the method further comprises the steps of:
   arranging the plurality of needles holding the plurality of cells such that the plurality of cell aggregates make contact with each other, so that the cell aggregates are fused with each other; and then
   pulling the needles out from the cell aggregates after the cell aggregates have fused with each other.

4. The method for producing a cell tissue structure according to claim 2, wherein
   the cell aggregates are arranged in the concave parts of the tray so that a predetermined cell tissue structure is obtained.

\* \* \* \* \*